United States Patent
Miller et al.

(10) Patent No.: US 6,495,823 B1
(45) Date of Patent: Dec. 17, 2002

(54) MICROMACHINED FIELD ASYMMETRIC ION MOBILITY FILTER AND DETECTION SYSTEM

(75) Inventors: Raanan A. Miller, Cambridge, MA (US); Erkinjon G. Nazarov, Las Cruces, NM (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 09/358,312

(22) Filed: Jul. 21, 1999

(51) Int. Cl.[7] .................... B01D 59/44; H01J 49/00
(52) U.S. Cl. .................... 250/286; 250/287; 250/288
(58) Field of Search .................... 250/281, 182, 250/286, 287, 288

(56) References Cited

U.S. PATENT DOCUMENTS

| | | | |
|---|---|---|---|
| 2,615,135 A | 10/1952 | Glenn | 250/41.9 |
| 2,818,507 A | 12/1957 | Britten | 250/41.9 |
| 2,919,348 A | 12/1959 | Bierman | 250/41.9 |
| 3,511,986 A | 5/1970 | Llewellyn | 250/41.9 |
| 3,619,605 A | 11/1971 | Cook et al. | 250/41.9 |
| 3,621,240 A | 11/1971 | Cohen et al. | 250/41.9 G |
| 3,648,046 A | 3/1972 | Denison et al. | 2250/41.9 DS |
| 4,019,989 A | 4/1977 | Hazewindus et al. | 250/396 ML |
| 4,163,151 A | 7/1979 | Bayless et al. | 250/296 |
| 4,167,668 A | 9/1979 | Mouriër | 250/291 |
| 4,315,153 A | 2/1982 | Vahrenkamp | 250/396 R |
| 4,517,462 A | 5/1985 | Boyer et al. | 250/286 |
| 4,761,545 A | 8/1988 | Marshall et al. | 250/291 |
| 4,885,500 A | 12/1989 | Hansen et al. | 313/256 |
| 4,931,640 A | 6/1990 | Marshall et al. | 250/291 |
| 5,019,706 A | 5/1991 | Allemann et al. | 250/291 |
| 5,047,723 A | 9/1991 | Puumalainen | 324/464 |
| 5,144,127 A | 9/1992 | Williams et al. | 250/287 |
| 5,281,494 A | 1/1994 | Chujian et al. | 250/292 |
| 5,298,745 A | 3/1994 | Kernan et al. | 250/292 |
| 5,373,157 A | 12/1994 | Hiroki et al. | 250/292 |
| 5,420,424 A | 5/1995 | Carnahan et al. | 250/287 |

(List continued on next page.)

FOREIGN PATENT DOCUMENTS

| | | |
|---|---|---|
| RU | 966583 | 10/1982 |
| RU | 1337934 A2 | 9/1987 |
| RU | 1627984 A2 | 2/1991 |
| RU | 1405489 A1 | 6/1998 |
| RU | 1412447 A1 | 6/1998 |
| RU | 1485808 A1 | 6/1998 |
| WO | WO 00/08454 | 2/2000 |
| WO | WO 00/08455 | 2/2000 |
| WO | WO 00/08456 | 2/2000 |
| WO | WO 00/08457 | 2/2000 |

OTHER PUBLICATIONS

By Buryakov et al., "Separation of ions according to mobility in a strong ac electric field", 1991 American Institute of Physics, Sov. Tech. Phys. Lett. 17(6), Jun. 1991, pp. 446 and 447.

By Carnahan et al., "Field Spectrometry—A New Analytical Technology for Trace Gas Analysis", ISA 1996,—Paper #96–009, pp. 87–96.

Russell Handy et al., "Determination of Nanomolar Levels of Perchlorate in Water by ESI–FAIMS–MS" Journal of Analytical Atomic Spectrometry, vol. 15, No. 8, p 907–911, Aug. 2000.

(List continued on next page.)

*Primary Examiner*—Bruce Anderson
(74) *Attorney, Agent, or Firm*—Hamilton, Brook, Smith and Reynolds, P.C.

(57) ABSTRACT

A micromechanical field asymmetric ion mobility filter for a detection system includes a pair of spaced substrates defining between them a flow path between a sample inlet and an outlet; an ion filter disposed in the path and including a pair of spaced filter electrodes, one electrode associated with each substrate; and an electrical controller for applying a bias voltage and an asymmetric periodic voltage across the ion filter electrodes for controlling the paths of ions through the filter.

82 Claims, 13 Drawing Sheets

U.S. PATENT DOCUMENTS

| | | | | |
|---|---|---|---|---|
| 5,455,417 A | * | 10/1995 | Sacristan | 250/287 |
| 5,492,867 A | | 2/1996 | Kotvas et al. | 437/228 |
| 5,536,939 A | * | 7/1996 | Freidhoff et al. | 250/281 |
| 5,541,408 A | | 7/1996 | Sittler | 250/288 |
| 5,644,131 A | | 7/1997 | Hansen | 250/292 |
| 5,654,544 A | | 8/1997 | Dresch | 250/287 |
| 5,723,861 A | | 3/1998 | Carnahan et al. | 250/287 |
| 5,736,739 A | | 4/1998 | Uber et al. | 250/287 |
| 5,763,876 A | * | 6/1998 | Michael et al. | 250/286 |
| 5,789,745 A | | 8/1998 | Martin et al. | 250/286 |
| 5,801,379 A | | 9/1998 | Kouznetsov | 250/286 |
| 5,834,771 A | | 11/1998 | Yoon et al. | 250/286 |
| 5,852,302 A | | 12/1998 | Hiraishi et al. | 250/292 |
| 5,965,882 A | * | 10/1999 | Megerie et al. | 250/287 |
| 6,049,052 A | | 4/2000 | Chutjian et al. | 219/69.12 |
| 6,051,832 A | * | 4/2000 | Fagan et al. | 250/286 |
| 6,124,592 A | * | 9/2000 | Spangler | 250/287 |
| 6,157,029 A | | 12/2000 | Chutjian et al. | 250/292 |
| 6,157,031 A | | 12/2000 | Prestage | 250/292 |
| 6,188,167 B1 | | 2/2001 | Chujian et al. | 250/292 |
| 6,262,416 B1 | | 7/2001 | Chutjian et al. | 250/292 |

OTHER PUBLICATIONS

Buryakov et al., "A New Method of Separation of Multi–atomic Ions by Mobility at Atmospheric Pressure Using a High–Frequency Amplitude–Asymmetric Strong Electric Field", 128 Int. J. of Mass Spectrometry and Ion Proc. 143–148 (1993).

Miller et al., "A Novel Micromachined High–Field Asymmetric Waveform Ion Mobility Spectrometer", Charles Stark Draper Laboratory, Department of Chemistry and Biochemistry (Oct. 10, 1999).

"A Micromachined Field Driven Radio Frequency–Ion Mobility Spectrometer for Trace Level Chemical Detection", A Draper Laboratory Proposal Against the "Advanced Cross–Enterprise Technology Develoopment for NASA Missions", Solicitation, NASA NRA 99–OSS–05.

Buryakov et al., "Drift Spectrometer for the Control of Amine Traces in the Atmosphere", 48 J. Anal. Chem. Issue 1, 156–165 (1993).

Handy et al., "Determination of Nanomolar Levels of Perchlorate in Water by ESI–FAIMS–MS", 15 J. Anal. At. Spectrometry, 907–911 (2000).

Buryakov et al., "Seperating Ions Based on Their Speed in Alternating Electric Fields in High Voltage", 17 Letters to JTF, Issue 12, 60–65 (Jun. 26, 1991).

Verenikov et al., "Analyzing Chemical Ingredients of Solution Using Ionic Gas Analysis", 127–133.

Buryalkov et al., "Devices and Methods of Gas Electro–fluorescents", 113–125.

Guevremont et al., "High Field Asymmetric Waveform Ion Mobility Spectrometry–Mass Spectrometry: An Investigation of Leucine Enkephalin Ions Produced by Electrospray Ionization." 10, J. Am. Soc. Mass Spectrom at 492–501 (1999).

E. Krylov, "A method of reducing diffusion losses in a drift spectrometer,"*Technical Physics*, vol. 44:1, pp. 113–116.

R. Guevremont, et al., "Atmospheric pressure ion focusing in a high–field asymmetric waveform ion mobility spectrometer," *Review of Scientific Instruments*, vol. 70:2, pp. 1370–1383.

* cited by examiner

180
MICROMACHINED FIELD ASYMMETRIC ION MOBILITY FILTER AND DETECTION SYSTEM

FIELD OF INVENTION

This invention relates to a Field Asymmetric Ion Mobility (FAIM) filter, and more particularly, to a micromachined FAIM filter and spectrometer.

BACKGROUND OF INVENTION

The ability to detect and identify explosives, drugs, chemical and biological agents as well as air quality has become increasingly more critical given increasing terrorist and military activities and environmental concerns. Previous detection of such agents was accomplished with conventional mass spectrometers, time of flight ion mobility spectrometers and conventionally machined FAIM spectrometers.

Mass spectrometers are very sensitive, highly selective and provide a fast response time. Mass spectrometers, however, are large and require significant amounts of power to operate. They also require a powerful vacuum pump to maintain a high vacuum in order to isolate the ions from neutral molecules and permit detection of the selected ions, and are also very expensive.

Another spectrometric technique which is less complex is time of flight ion mobility spectrometry which is the method currently implemented in most portable chemical weapons and explosives detectors. The detection is based not solely on mass, but on charge and cross-section of the molecule as well. However, because of these different characteristics, molecular species identification is not as conclusive and accurate as the mass spectrometer. Time of flight ion mobility spectrometers typically have unacceptable resolution and sensitivity limitations when attempting to reduce their size, that is a drift tube length less than 2 inches. In time of flight ion mobility, the resolution is proportional to the length of the drift tube. The longer the tube the better the resolution, provided the drift tube is also wide enough to prevent all ions from being lost to the side walls due to diffusion. Thus, fundamentally, miniaturization of time of flight ion mobility systems leads to a degradation in system performance. While these devices are relatively inexpensive and reliable, they suffer from several limitations. First, the sample volume through the detector is small, so to increase spectrometer sensitivity either the detector electronics must have extremely high sensitivity, requiring expensive electronics, or a concentrator is required, adding to system complexity. In addition, a gate and gating electronics are usually needed to control the injection of ions into the drift tube.

FAIM spectrometry was developed in the former Soviet Union in the 1980's. FAIM spectrometry allows a selected ion to pass through a filter while blocking the passage of undesirable ions. Conventional FAIM spectrometers are large and expensive, e.g., the entire device is nearly a cubic foot in size and costs over $25,000. These systems are not suitable for use in applications requiring small detectors. They are also relatively slow, taking as much as one minute to produce a complete spectrum of the sample gas, are difficult to manufacture and are not mass producible.

BRIEF SUMMARY OF THE INVENTION

It is therefore an object of this invention to provide a FAIM filter and detection system which can more quickly and accurately control the flow of selected ions to produce a sample spectrum than conventional FAIM devices.

It is a further object of this invention to provide such a filter and detection system which can detect multiple preselected ions without having to sweep the bias voltage.

It is a further object of this invention to provide such a filter and detection system which can even detect selected ions without a bias voltage.

It is a further object of this invention to provide such a filter and detection system which can detect ions spatially based on the ions' trajectories.

It is a further object of this invention to provide such a filter and detection system which has a very high resolution.

It is a further object of this invention to provide such a filter and detection system which can detect selected ions faster than conventional detection devices.

It is a further object of this invention to provide such a filter and detection system which has a sensitivity of parts per billion to parts per trillion.

It is a further object of this invention to provide such a filter and detection system which may be packaged in a single chip.

It is further object of this invention to provide such filter and detection system which is cost effective to implement and produce.

The invention results from the realization that an extremely small, accurate and fast FAIM filter and detection system can be achieved by defining a flow path between a sample inlet and an outlet using a pair of spaced substrates and disposing an ion filter within the flow path, the filter including a pair of spaced electrodes, one electrode associated with each substrate and a controller for selectively applying a bias voltage and an asymmetric periodic voltage across the electrodes to control the path of ions through the filter.

The invention results from the further realization that by providing an array of filters, each filter associated with a different bias voltage, the filter may be used to detect multiple selected ions without sweeping the bias voltage.

The invention results from the further realization that by varying the duty cycle of the periodic voltage, no bias voltage is required.

The invention results from the further realization that by segmenting the detector, ion detection may be achieved with greater accuracy and resolution by detecting ions spatially according to the ions' trajectories as the ions exit the filter.

This invention features a micromechanical field asymmetric ion mobility filter for a detection system. There is a pair of spaced substrates defining between them a flow path between a sample inlet and an outlet, an ion filter disposed in the path and including a pair of spaced filter electrodes, one electrode associated with each substrate and an electrical controller for applying a bias voltage and an asymmetric periodic voltage across the ion filter electrodes for controlling the paths of ions through the filter.

In a preferred embodiment there may be a detector, downstream from the ion filter, for detecting ions that exit the filter. The detector may include a plurality of segments, the segments separated along the flow path to spatially separate the ions according to their trajectories. There may be confining electrodes, responsive to the electrical controller, for concentrating selected ions as they pass through the filter. The confining electrodes may be silicon. The silicon electrodes may act as spaces for spacing the substrates. There may be a heater for heating the flow path. The heater may include the ion filter electrodes. The electrical controller may include means for selectively applying a current through the filter electrodes to heat the filter electrodes. The substrate may be glass. The glass may be Pyrex®. There may be an ionization source, upstream from the filter, for ionizing a fluid flow from the sample inlet. The ionization source may include a radioactive source. The ionization source may include an ultraviolet lamp. The ionization source may include a corona discharge device. There may be a clean air inlet for introducing purified air into the flow path. There may be a pump in communication with the flow path, for regulating a fluid flow through the flow path.

The invention also features a field asymmetric ion mobility filter and detection system. There is a housing having a flow path between a sample inlet and an outlet, an ion filter disposed in the flow path and including a pair of spaced filter electrodes, an electrical controller for applying a bias voltage and an asymmetric periodic voltage across the ion filter electrodes for controlling the path of ions through the filter, and a segmented detector, downstream from the ion filter, its segments separated along the flow path to spatially separate the ions according to their trajectories.

In a preferred embodiment there may be confining electrodes, responsive to the electrical controller, for concentrating the ions as they pass through the filter. The confining electrode may be silicon. The silicon electrodes may act as a spacer for spacing the filter electrodes. There may be a heater for heating the flow path. The heater may include the ion filter electrodes. The electrical controller may includes means for selectively applying current through the filter electrodes to heat the filter electrodes. There may be an ionization source upstream from the filter for ionizing fluid flow from the sample inlet. The ionization source may include a radioactive source. The ionization source may include an ultraviolet lamp. The ionization source may include a corona discharge device. There may be a clean air inlet for introducing purified air into the flow path. There may be a pump in communication with the flow path for regulating a fluid flow through the flow path.

The invention also features a field asymmetric ion mobility filter array. There is a housing defining at least one flow path between a sample inlet and an outlet, a plurality of ion filters disposed within the housing, each ion filter including a pair spaced filter electrodes, and an electrical controller for applying a bias voltage and an asymmetric periodic voltage across each pair of ion filter electrodes for controlling the path of ions through each filter.

In a preferred embodiment each ion filter may be associated with one of the flow paths. There may be a detector downstream from each ion filter for detecting ions that exit each said filter. Each detector may include a plurality of segments, the segments separated along the flow path to spatially separate the ions according to their trajectories. There may be a plurality of confining electrodes, responsive to the electrical controller, for concentrating the ions as they pass through each filter. Each confining electrode may be silicon. The silicon electrode may act as a spacer for spacing the filter electrodes. There may be a heater for heating the at least one flow path. The heater may include each pair of ion filter electrodes. The electrical controller may include means for selectively applying a current through each pair of filter electrodes to heat the filter electrodes. There may be an ionization source upstream from each filter for ionizing a fluid flow from the sample inlet. The ionization source may be a radioactive source. The ionization source may be an ultraviolet lamp. The ionization source may be a corona discharge device. There may be a clean air inlet for introducing purified air into the at least one flow path. There may be a pump in communication with each flow path for regulating a fluid flow through each flow path.

The invention also features an uncompensated field asymmetric ion mobility filter for a detection system. There is a housing having a flow path between a sample inlet and an outlet, an ion filter disposed in the path and including a pair of spaced filter electrodes, an electrical controller for applying an uncompensated asymmetric periodic voltage across the ion filter for controlling the path of ions through the ion filter, and a selection circuit for selectively adjusting the duty cycle of the periodic voltage to target a selected specie or species of ion to be detected.

In a preferred embodiment there may be a detector downstream from the ion filter for detecting ions that exit the filter. The detector may include a plurality of segments, the segments separated along the flow path to spatially separate the ions according to their trajectories. There may be a confining electrode, responsive to the electrical controller, for concentrating the ions as they pass through the filter. The confining electrode may be silicon. The silicon electrode may act as a spacer for spacing the filter electrodes. There may be a heater for heating the flow path. The heater may include the ion filter electrodes. The electrical controller may include means for selectively applying a current through the filter electrodes to heat the filter electrodes. There may be an ionization source, upstream from the filter, for ionizing a fluid flow from sample inlet. The ionization source may include a radioactive source. The ionization source may include an ultraviolet lamp. The ionization source may include a corona discharge device. There may be a clean air inlet for introducing purified air into the flow path. There may be a pump in communication with the flow path for regulating a fluid flow through the flow path.

The invention also features a field asymmetric ion mobility filter. There is a housing having a flow path between a sample inlet and an outlet, an ion filter disposed in the flow path and including a pair of spaced filter electrodes, a pair of confining electrodes transverse to the flow path, and an electrical controller for applying a first bias voltage and an asymmetric periodic voltage across the ion filter electrodes and for applying a second bias voltage across the confining electrodes for controlling the path of ions through the filter.

In a preferred embodiment there may be a detector downstream from the ion filter for detecting ions that exit the filter. The detector may include a plurality of segments, the segments separated along the flow path to spatially separate the ions according to their trajectories. The confining electrodes may be silicon. The silicon electrodes may act as a spacer for spacing the filter electrodes. There may be a heater for heating the flow path. The heater may include the ion filter electrodes. The heater may include the confining electrodes. The electrical controller may include means for selectively applying a current through the filter electrodes to heat the filter electrodes. The electrical controller may include means for selectively applying a current through the confining electrodes to heat the confining electrodes. There may be an ionization source upstream from the filter for ionizing fluid flow from the sample inlet. The ionization source may include a radiation source. The ionization source may include an ultraviolet lamp. The ionization source may be a corona discharge device. There may be a clean air inlet for introducing purified air into the flow path. There may be a pump in communication with the flow path for regulating a fluid flow through the flow path.

BRIEF DESCRIPTION OF THE DRAWINGS

Other objects, features and advantages will occur to those skilled in the art from the following description of a preferred embodiment and the accompanying drawings, in which.

PREFERRED EMBODIMENT

Figure 1:
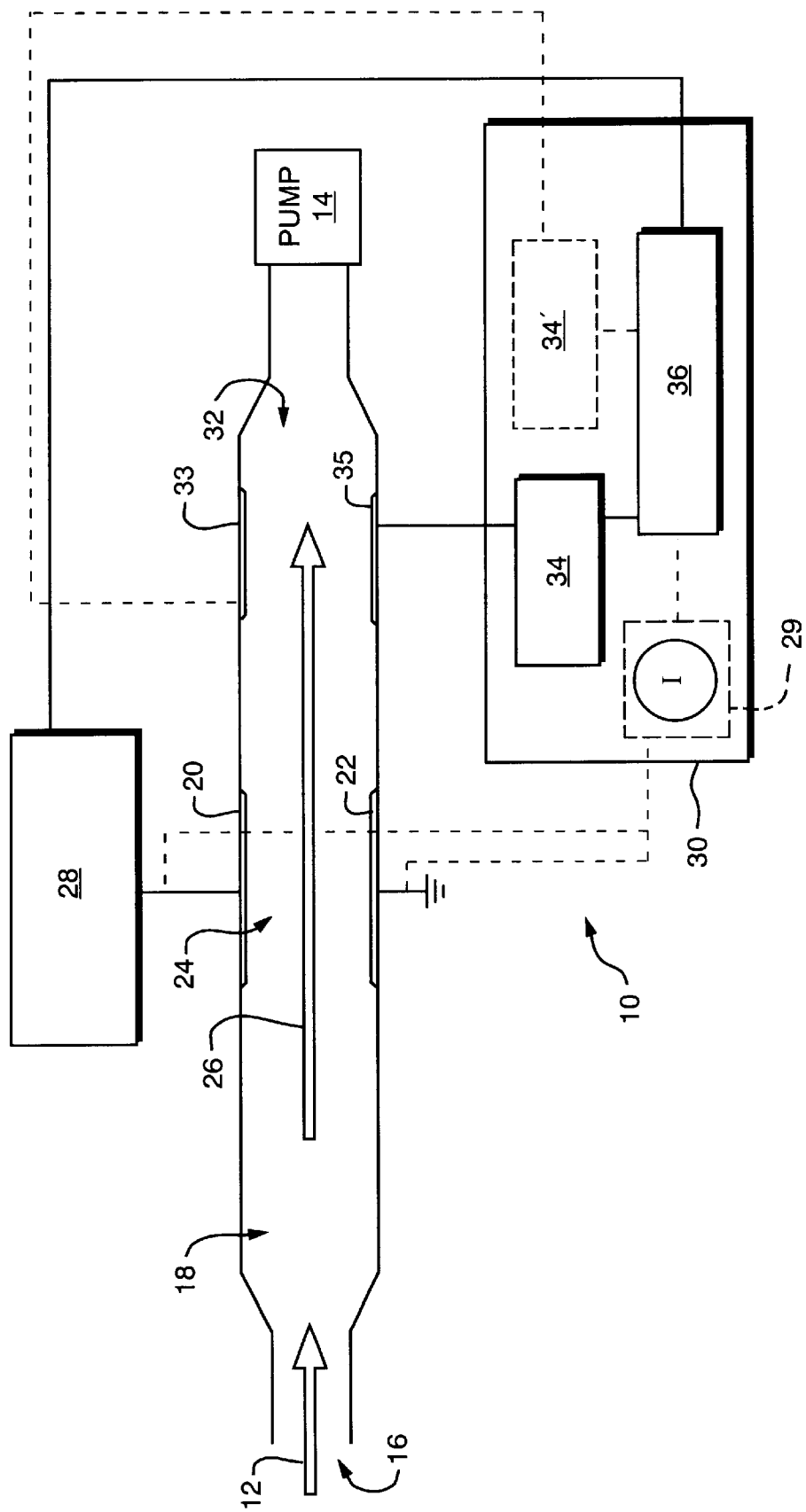
FIG. 1 is a schematic block diagram of the micromachined filter and detection system according to the present invention.

FAIM spectrometer 10, FIG. 1, operates by drawing a gas, indicated by arrow 12, via pump 14, through inlet 16 into ionization region 18. The ionized gas is passed between parallel electrode plates 20 and 22, which comprise ion filter 24, following flow path 26. As the gas ions pass between plates 20 and 22, they are exposed to an asymmetric oscillating electric field between electrode plates 20 and 22 induced by a voltage applied to the plates by voltage generator 28 in response to electronic controller 30.

As ions pass through filter 24, some are neutralized by plates 20 and 22 while others pass through and are sensed by detector 32. Detector 32 includes a top electrode 33 at a predetermined voltage and a bottom electrode 35, typically at ground. Top electrode 33 deflects ions downward to electrode 35. However, either electrode may detect ions depending on the ion and the voltage applied to the electrodes. Moreover, multiple ions may be detected by using top electrode 33 as one detector and bottom electrode 35 as a second detector. Electronic controller 30 may include, for example, amplifier 34 and microprocessor 36. Amplifier 34 amplifies the output of detector 32, which is a function of the charge collected by detector 34, and provides the output to microprocessor 36 for analysis. Similarly, amplifier 34', shown in phantom, may be provided where electrode 33 is also utilized as a detector.

Figure 2:
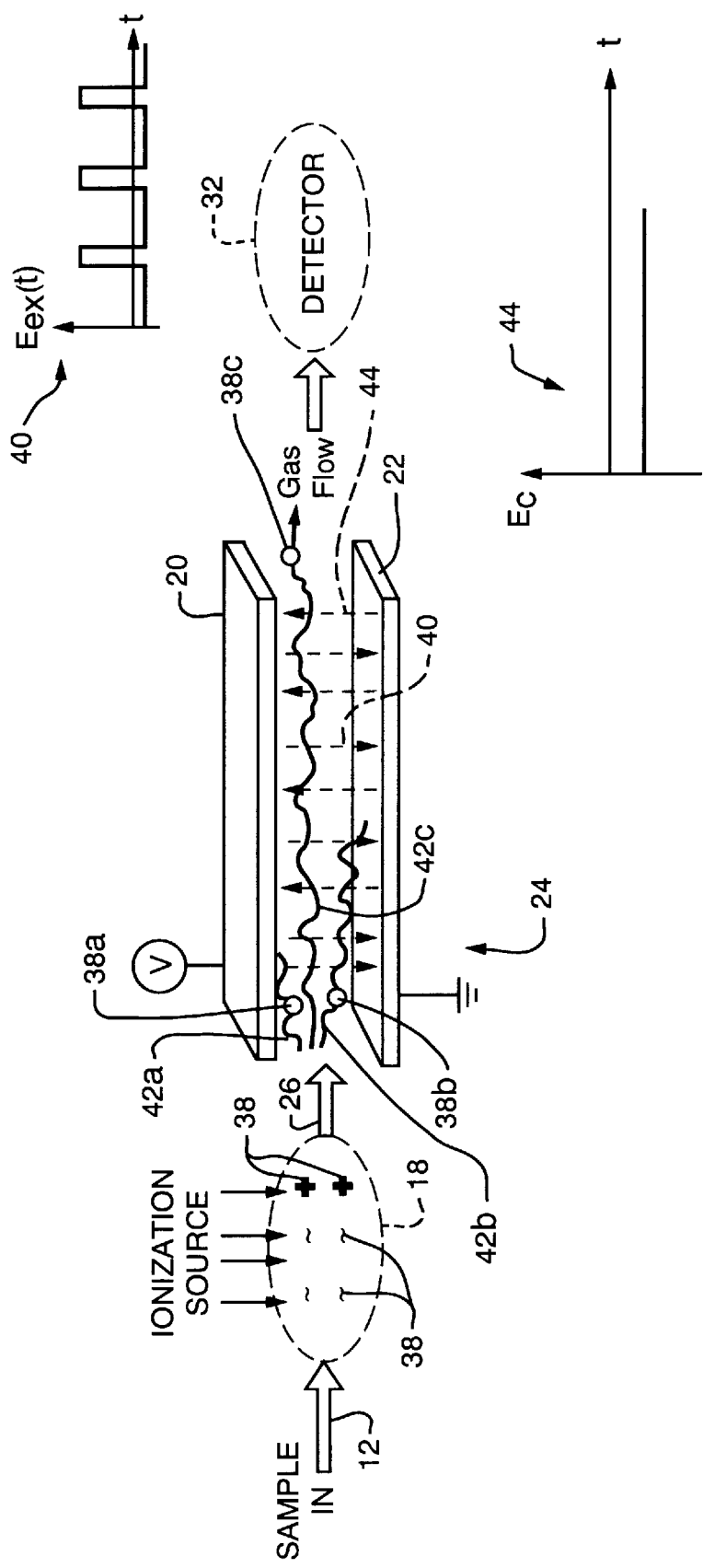
FIG. 2 is a schematic representation of the ions as they pass through the filter electrodes of FIG. 1 toward the detector.

As ions 38, FIG. 2, pass through alternating asymmetric electric field 40, which is transverse to gas flow 12, electric field 40 causes the ions to "wiggle" along paths 42a, 42b and 42c. Field 40 is typically in the range of ±(1000–2000) volts dc and has a maximum field strength of 40,000 V/cm. The path taken by a particular ion is a function of its mass, size, cross-section and charge. Once an ion reaches electrode 20 or 22, it is neutralized. A second, bias or compensation field 44, typically in the range of ±2000 V/cm or ±100 volts dc, is concurrently induced between electrodes 20 and 22 by a bias voltage applied to plates 20 and 22, also by voltage generator 28, FIG. 1, in response to microprocessor 36 to enable a preselected ion species to pass through filter 24 to detector 32. Compensation field 44 is a constant bias which offsets alternating asymmetric field 40 to allow the preselected ions, such as ion 38c to pass to detector 32. Thus, with the proper bias voltage, a particular species of ion will follow path 42c while undesirable ions will follow paths 42a and 42b to be neutralized as they encounter electrode plates 20 and 22.

The output of FAIM spectrometer 10 is a measure of the amount of charge on detector 32 for a given bias voltage 44. The longer filter 24 is set at a given compensation bias voltage, the more charge will accumulate on detector 32. However, by sweeping compensation voltage 44 over a predetermined voltage range, a complete spectrum for sample gas 12 can be achieved. The FAIM spectrometer according to the present invention requires typically less than thirty seconds and as little as one second to produce a complete spectrum for a given gas sample.

Figure 3A:
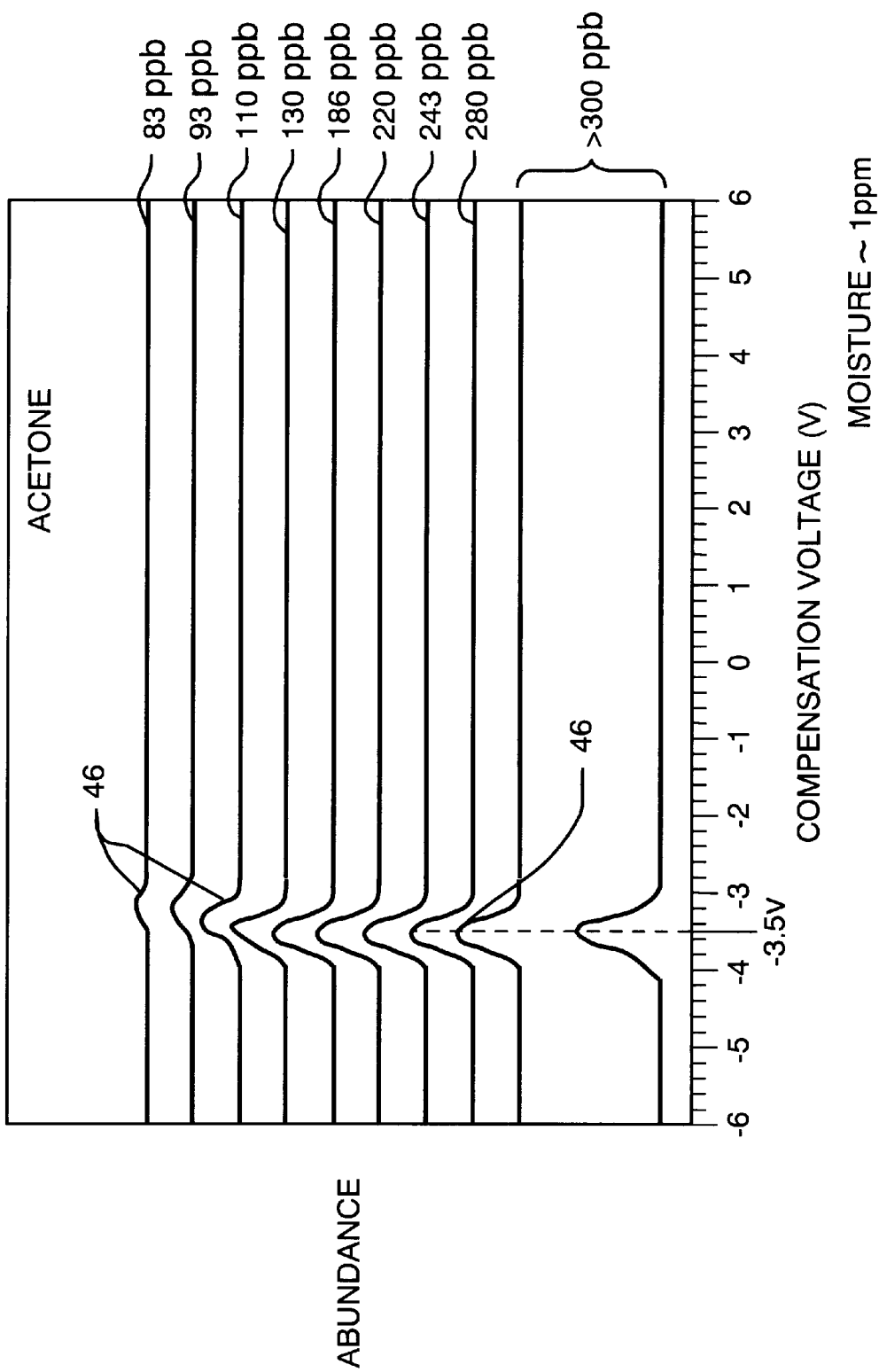
FIG. 3A is a graphical representation of the bias voltage required to detect acetone and the sensitivity obtainable.
Figure 3B:
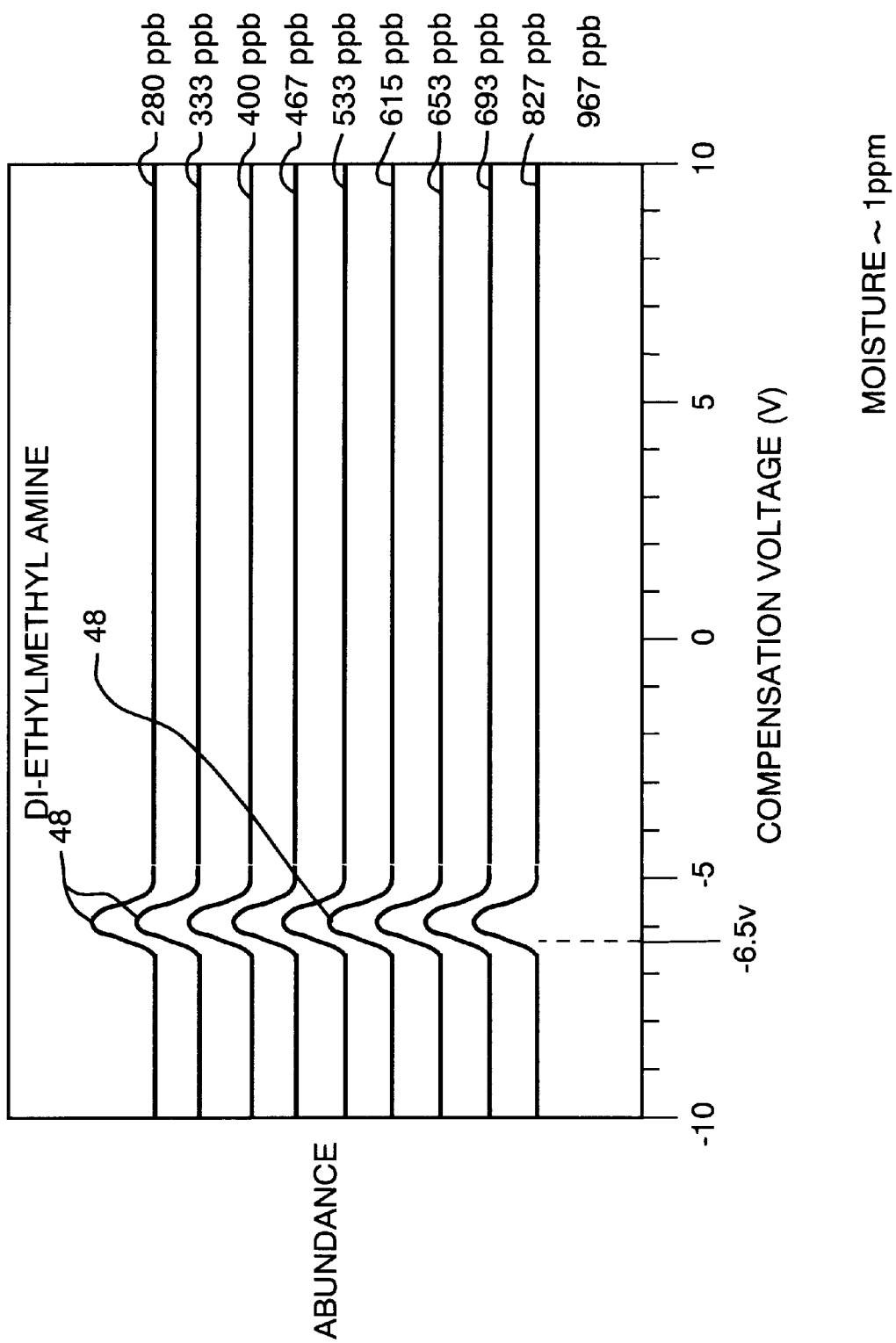
FIG. 3B is a representation, similar to FIG. 3A, of the bias voltage required to detect Diethyl methyl amine.

By varying compensation bias voltage 44 the species to be detected can be varied to provide a complete spectrum of the gas sample. For example, with a bias voltage of −3.5 volts acetone was detected as demonstrated by concentration peaks 46, FIG. 3A in concentrations as low as 83 parts per billion. In contrast, at a bias voltage of −6.5 volts, diethyl methyl amine, peaks 48, FIG. 3B, was detected in concentrations as low as 280 parts per billion.

Figure 4:
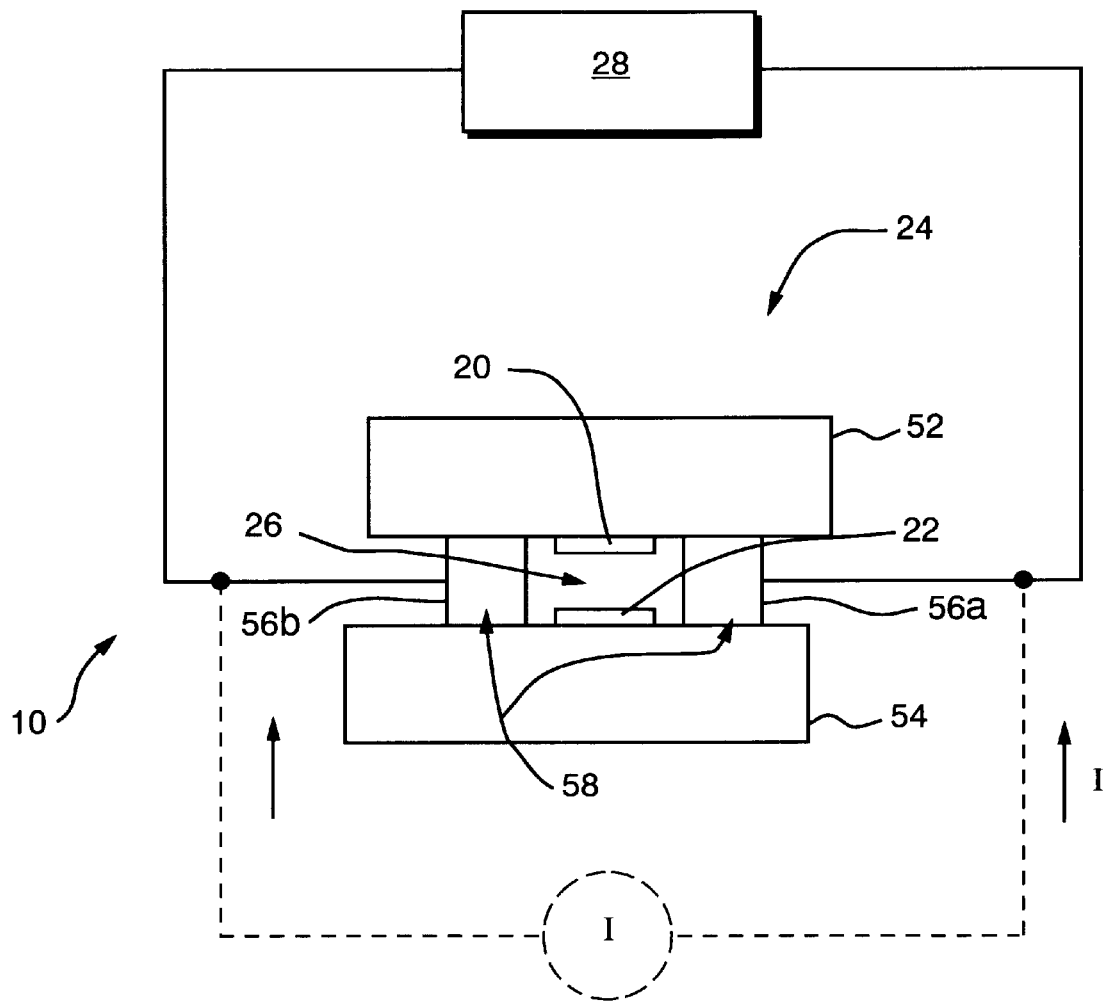
FIG. 4 is a cross sectional of the view of the spaced, micromachined filter according to the present invention.

Filter 24, FIG. 4, is on the order of one inch in size. Spectrometer 10 includes spaced substrates 52 and 54, for example glass such as Pyrex® available from Corning Glass, Corning, N.Y., and electrodes 20 and 22, which may be example gold, titanium, or platinum, mounted or formed on substrates 52 and 54, respectively. Substrates 52 and 54 are separated by spacers 56a and 56b which may be formed by etching or dicing silicon wafer. The thickness of spacers 56a–b defines the distance between electrodes 20 and 22. Moreover, applying the same voltage to silicon spacers 56a and 56b, typically ±(10–1000 volts dc) transforms spacers 56a and 56b into electrodes which produce a confining electric field 58, which guides or confines the ions' paths to the center of flow path 26, FIG. 1, in order to obtain a better sample spectrum. To confine the ions, spacer electrodes 56a-b must be at the same voltage so as to "push" the ions to the center of flow path 26. This increases the sensitivity of the system by preserving more ions so that more ions strike detector 32. However, this is not a necessary limitation of the invention.

To maintain accurate and reliable operation of spectrometer 10, neutralized ions which accumulate on electrode plates 20 and 22 must be purged. This may be accomplished by heating flow path 26. For example, controller 30, FIG. 1, may include current source 29, shown in phantom, which provides, in response to microprocessor 36, a current I to electrode plates 20 and 22 to heat the plates, removing accumulated molecules. Similarly, current I may instead be applied to spacer electrodes 56a and 56 b, FIG. 4, to heat flow path 26 and clean plates 20 and 22.

Figure 5:
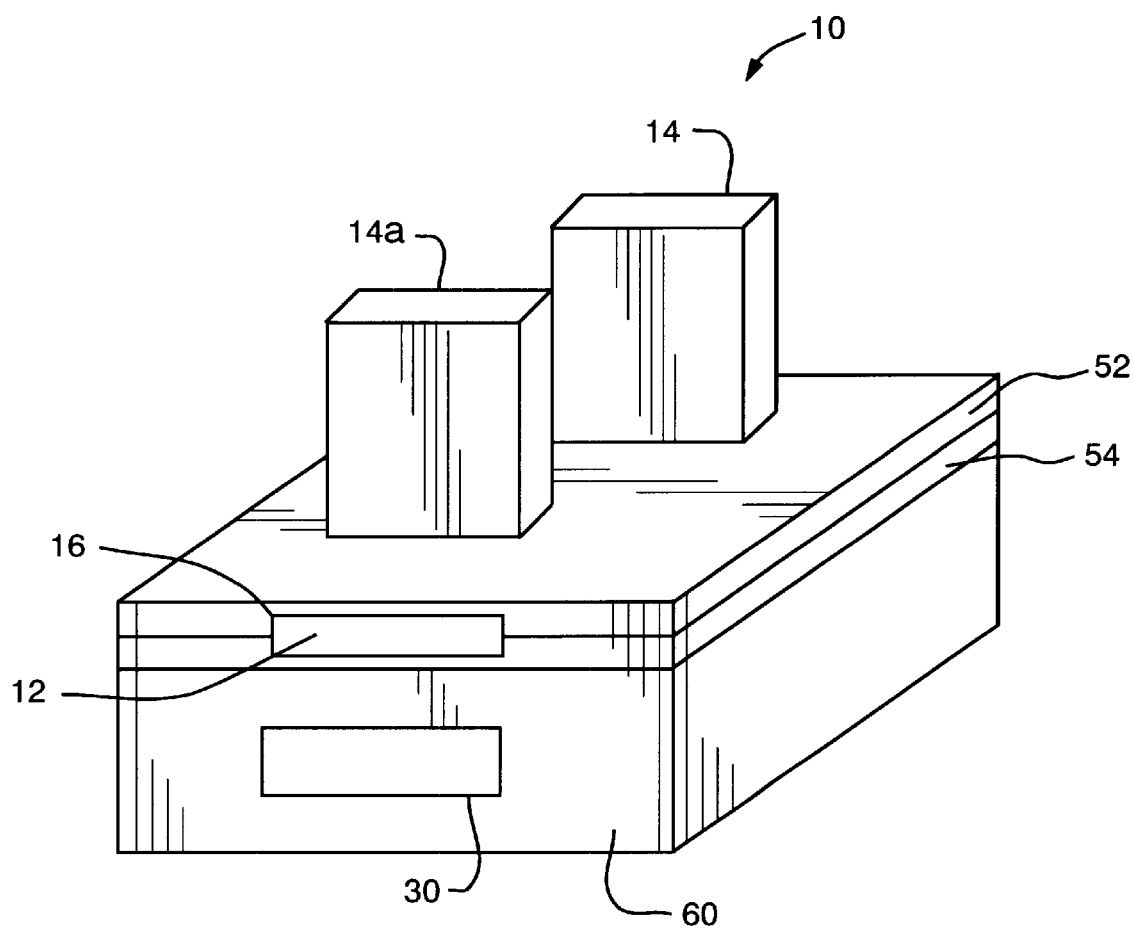
FIG. 5 is a three dimensional view of the packaged micromachined filter and detection system, including fluid flow pumps, demonstrating the miniaturized size which maybe realized.

Packaged FAIM spectrometer 10, FIG. 5, may be reduced in size to one inch by one inch by one inch. Pump 14 is mounted on substrate 52 for drawing a gas sample 12 into inlet 16. Clean dry air may be introduced into flow path 26, FIG. 1, by recirculation pump 14a prior to or after ionization of the gas sample. Electronic controller 30 may be etched into silicon control layer 60 which combines with substrates 52 and 54 to form a housing for spectrometer 10. Substrates 52 and 54 and control layer 60 may be bonded together, for example, using anodic bonding, to provide an extremely small FAIM spectrometer. Micro pumps 14 and 14a provide a high volume throughput which further expedites the analysis of gas sample 12. Pumps 14 and 14a may be, for example, conventional miniature disk drive motors fitted with small centrifugal air compressor rotors or micromachined pumps, which produce flow rates of 1 to 4 liters per minute. One example of pump 14 is available from Sensidyne, Inc., Clearwater, Fla.

Figure 6:
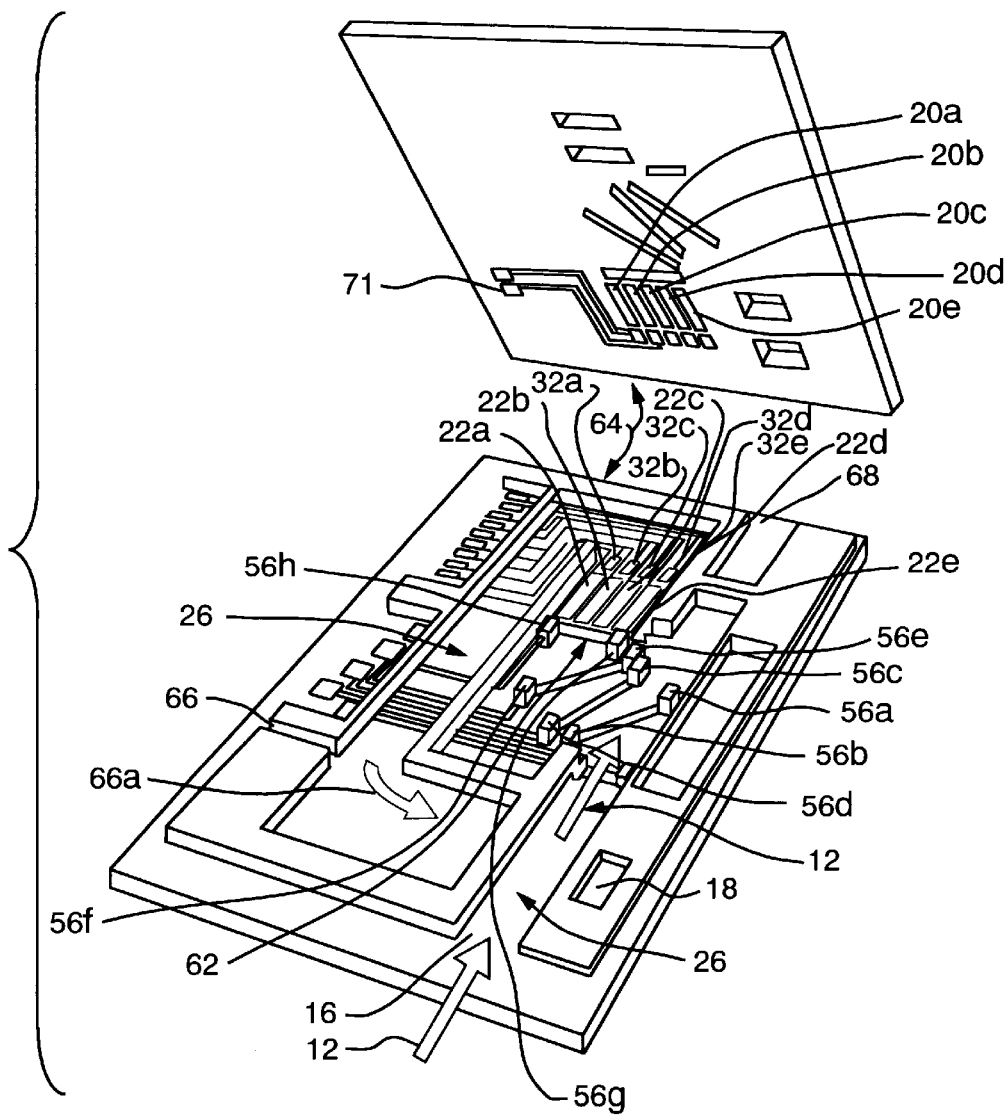
FIG. 6 is an exploded view of one embodiment according to the present invention in which an array of filters and detectors are disposed in a single flow path.

While the FAIM spectrometer according to the present invention quickly produces a spectrum for a particular gas sample, the time for doing so may be further reduced with an array of filters. FAIM spectrometer 10, FIG. 6, may include filter array 62, a single inlet 16 and single flow path 26. Sample gas 12 is guided by confining electrodes 56a-h to filter array 62 after passing by ionization source 18, which may include an ultraviolet light source, a radioactive device or corona discharge device. Filter array 62 includes, for example, paired filter electrodes 20a–e and 22a–e and may simultaneously detect different ion species by applying a different compensation bias voltage 44, FIG. 2, to each electrode pair and sweeping each electrode pair over a different voltage range greatly reducing the sweep time. However, array 62 may include any number of filters depending on the size of the spectrometer. Detector array 64, which includes detectors 32a–e, detects multiple selected ion species simultaneously, thereby reduce the time necessary to obtain a spectrum of the gas sample 12. The electrode pairs share the same asymmetric periodic ac voltage 40.

Clean dry air may be introduced into flow path 26 through clean air inlet 66 via recirculator pump 14a, FIG. 5. Drawing in clean dry air assists in reducing the FAIM spectrometer's sensitivity to humidity. Moreover, if the spectrometer is operated without clean dry air and a known gas sample is introduced into the device, the device can be used as a humidity sensor since the resulting spectrum will change with moisture concentration from the standardized spectrum for the given sample.

Figure 7:
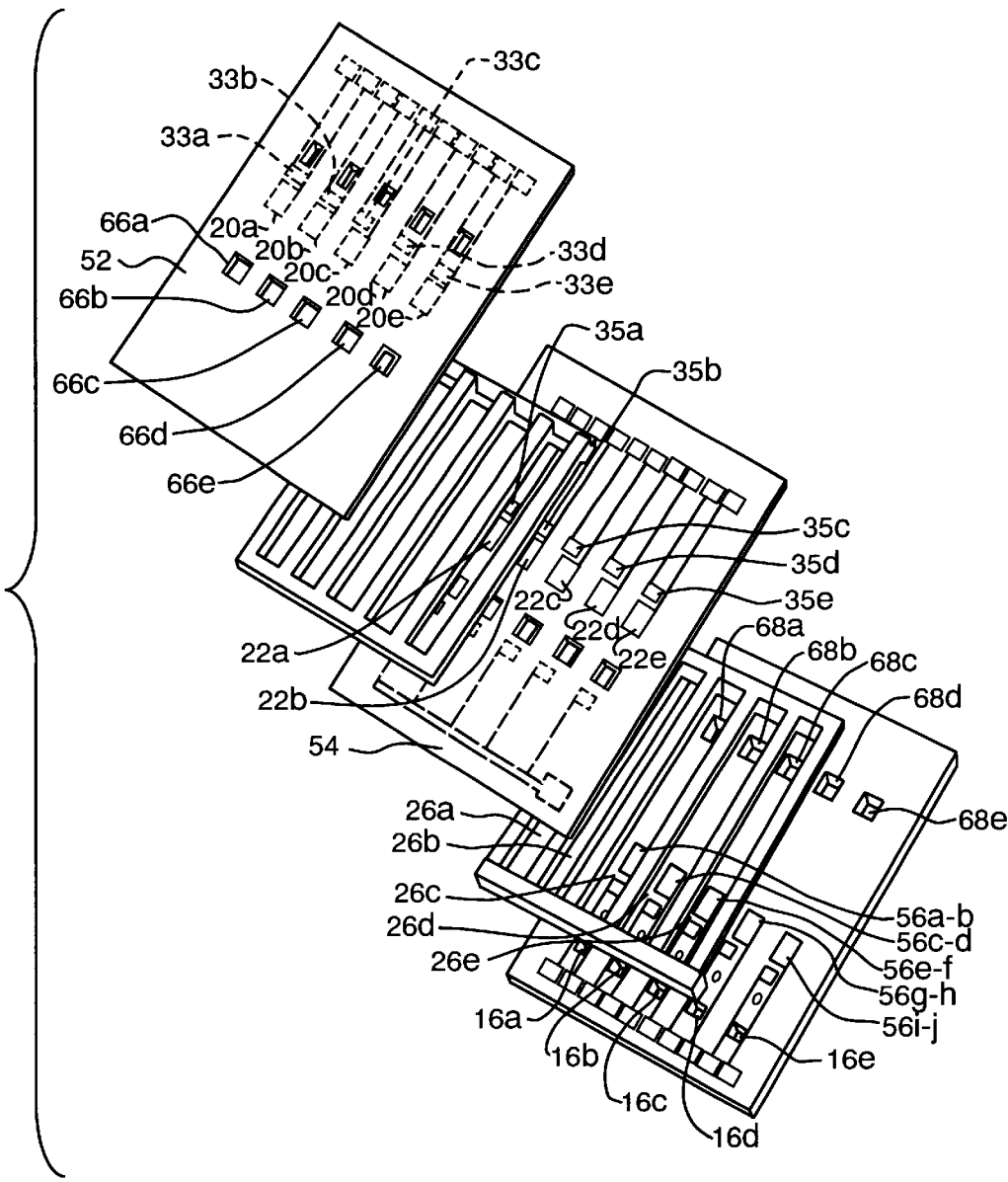
FIG. 7 is an exploded view, similar to FIG. 6, in which the array of filters is stacked and one filter and detector is associated with a single flow path.

However, rather than each filter of filter array 62 sharing the same flow path 26, individual flow paths 26a–e, FIG. 7, may be provided so that each flow path has associated with it, for example, inlet 16a , ionization region 18a, confining electrodes 56a, 56b, ion filter electrode pair 20a, 22a, detector electrode pair 33a, 35a and exit port 68a.

Figure 8:
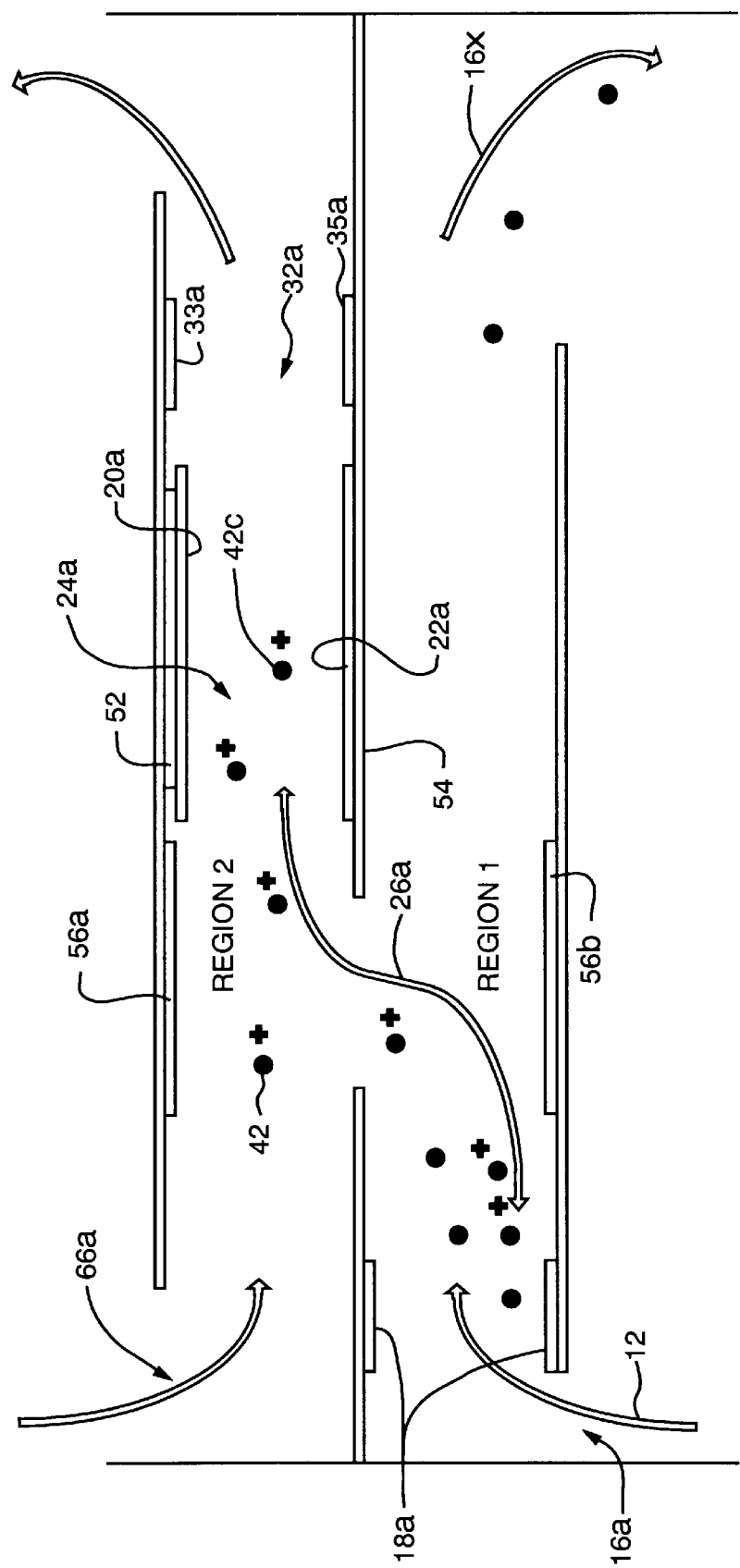
FIG. 8 is a cross sectional representation of a single flow path of the arrayed filter and detector system of FIG. 7.

In operation, sample gas 12 enters sample inlet 16a, FIG. 8, and is ionized by, for example, a corona discharge device 18a. The ionized sample is guided towards ion filter 24a by confining electrodes 56a, 56b. As ions pass between ion filter electrodes 20a and 22a, undesirable ions will be neutralized while selected ions will pass through filter 24a to be detected by detector 32a.

Figure 9:
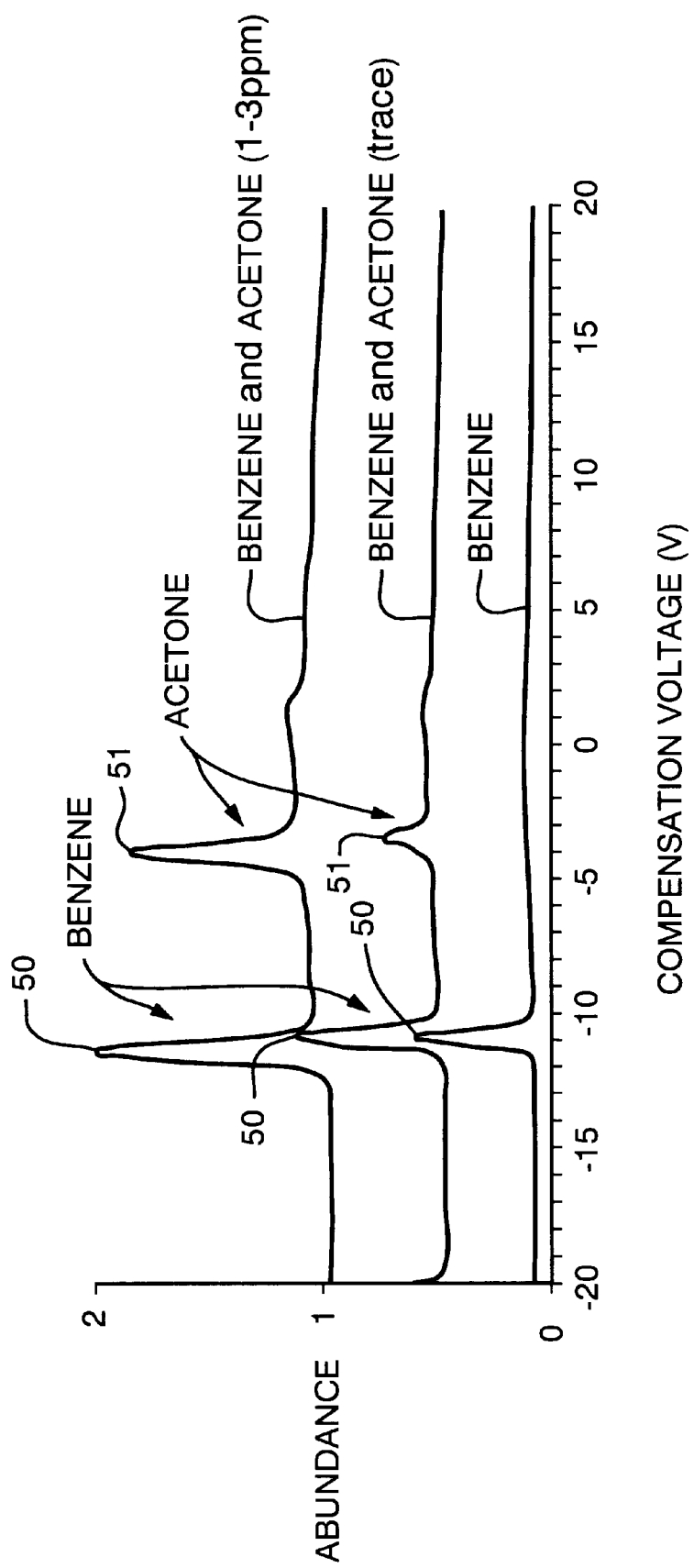
FIG. 9 is graphical representation demonstrating simultaneous multiple detections of benzene and acetone.

As shown in FIG. 9, multiple, simultaneous detections were made of Benzene, peaks 50 and acetone peaks 51, demonstrating the advantage of the arrayed filters and detectors according to the present invention.

Figure 10:
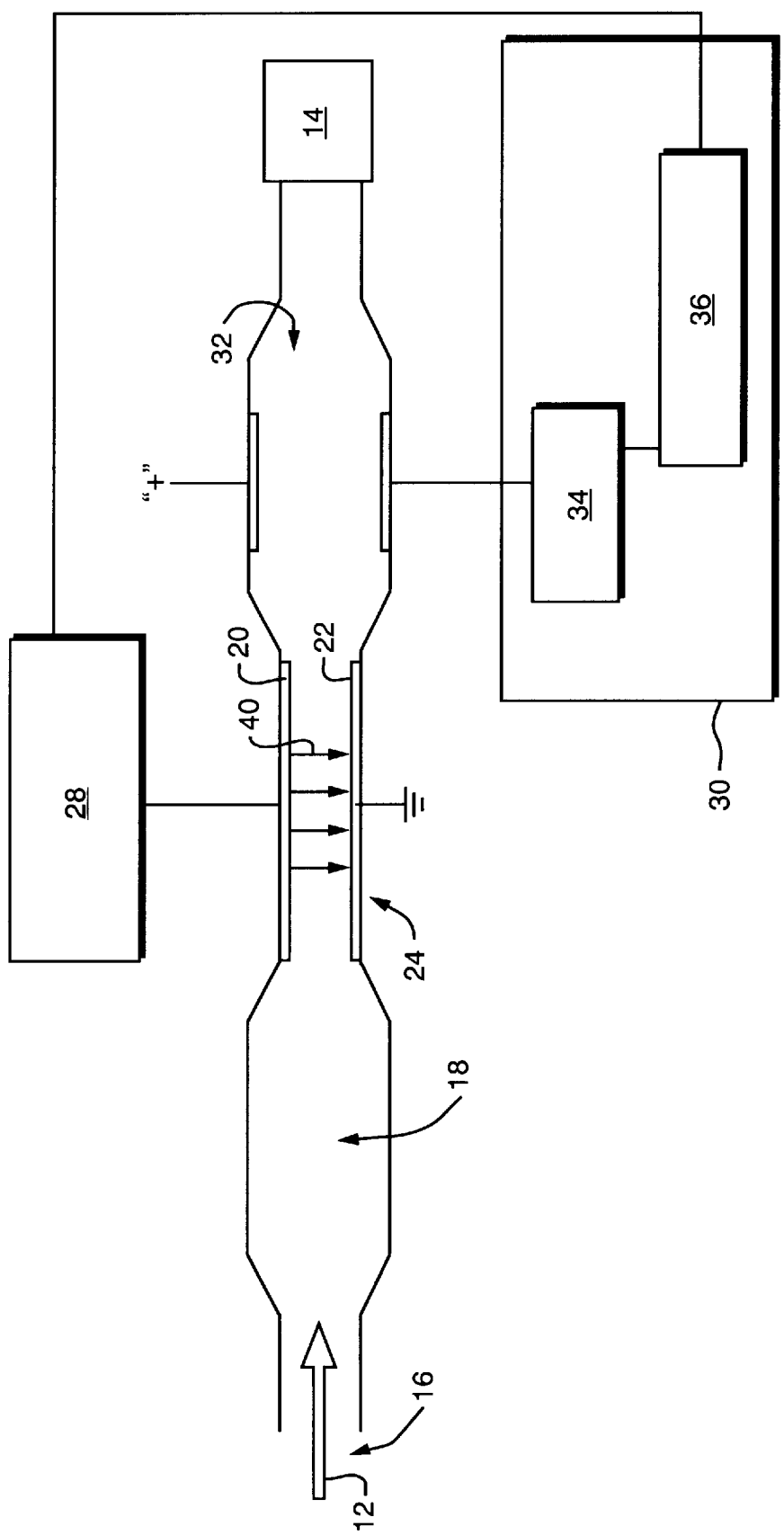
FIG. 10 is a schematic block diagram, similar FIG. 1, in which the filter is not compensated by a bias voltage and the duty cycle of the periodic voltage is instead varied to control the flow of ions through the filter.
Figure 11:
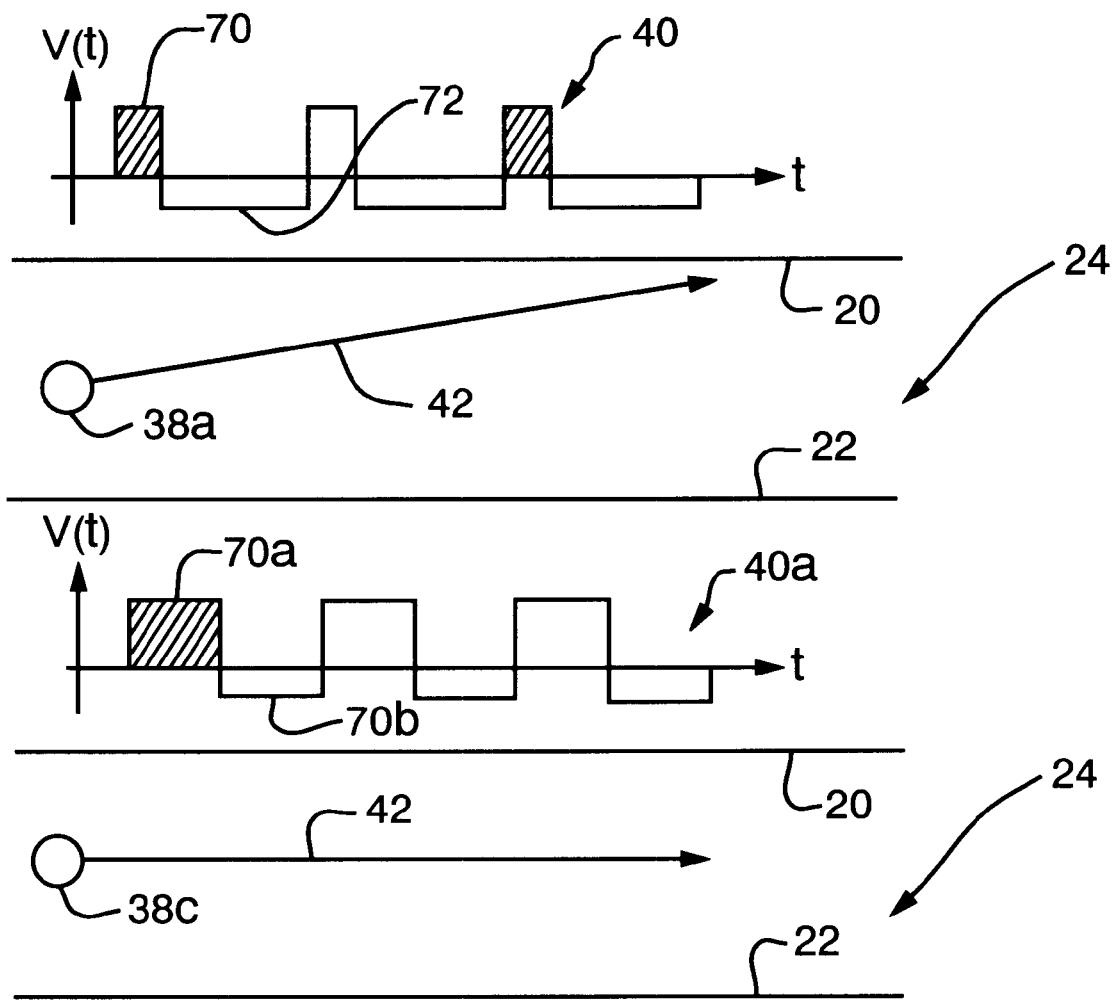
FIG. 11 is a graphical representation of an asymmetric periodic voltage having a varying duty cycle which is applied to the filter of FIG. 9 to filter selected ions without a bias voltage.

It has also been found that a compensation bias voltage is not necessary to detect a selected specie or species of ion. By varying the duty cycle of the asymmetric periodic voltage applied to electrodes 20 and 22 of filter 24, FIG. 10, there is no need to apply a constant bias voltage to plate electrodes 20 and 22. Voltage generator 28, in response to control electronics 30 varies the duty cycle of asymmetric alternating voltage 40. By varying the duty cycle of periodic voltage 40, FIG. 11, the path of selected ion 32c may be controlled. As an example, rather than a limitation, the duty cycle of field 40 may be one quarter: 25% high, peak 70, and 75% low, valley 72, and ion 38c approaches plate 20 to be neutralized. However, by varying the duty cycle of voltage 40a to 40%, peak 70a, ion 38c passes through plates 20 and 22 without being neutralized. Typically the duty cycle is variable from 10–50% high and 90–50% low. Accordingly, by varying the duty cycle of field 40, an ion's path may be controlled without the need of a bias voltage.

Figure 12:
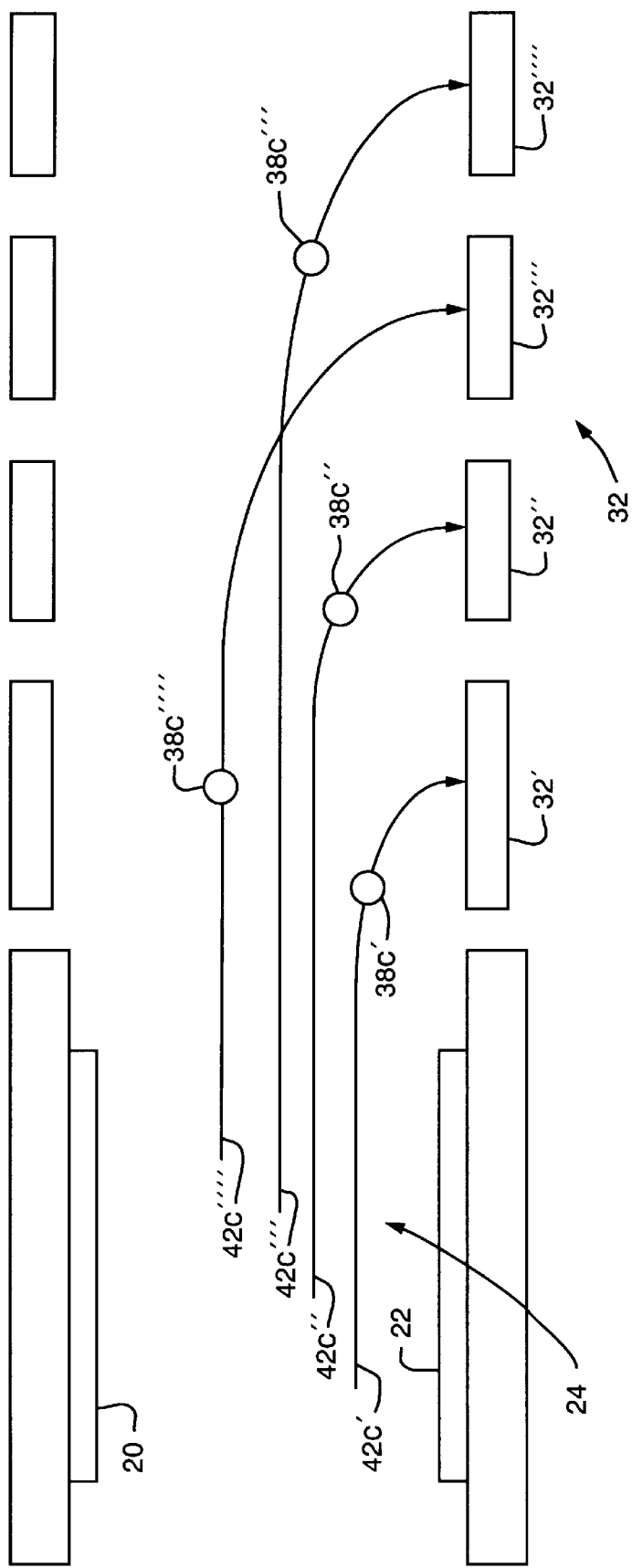
FIG. 12 is a schematic diagram of a filter and detector system in which the detector is segmented to spatially detect ions as they exit the filter.
Figure 7:
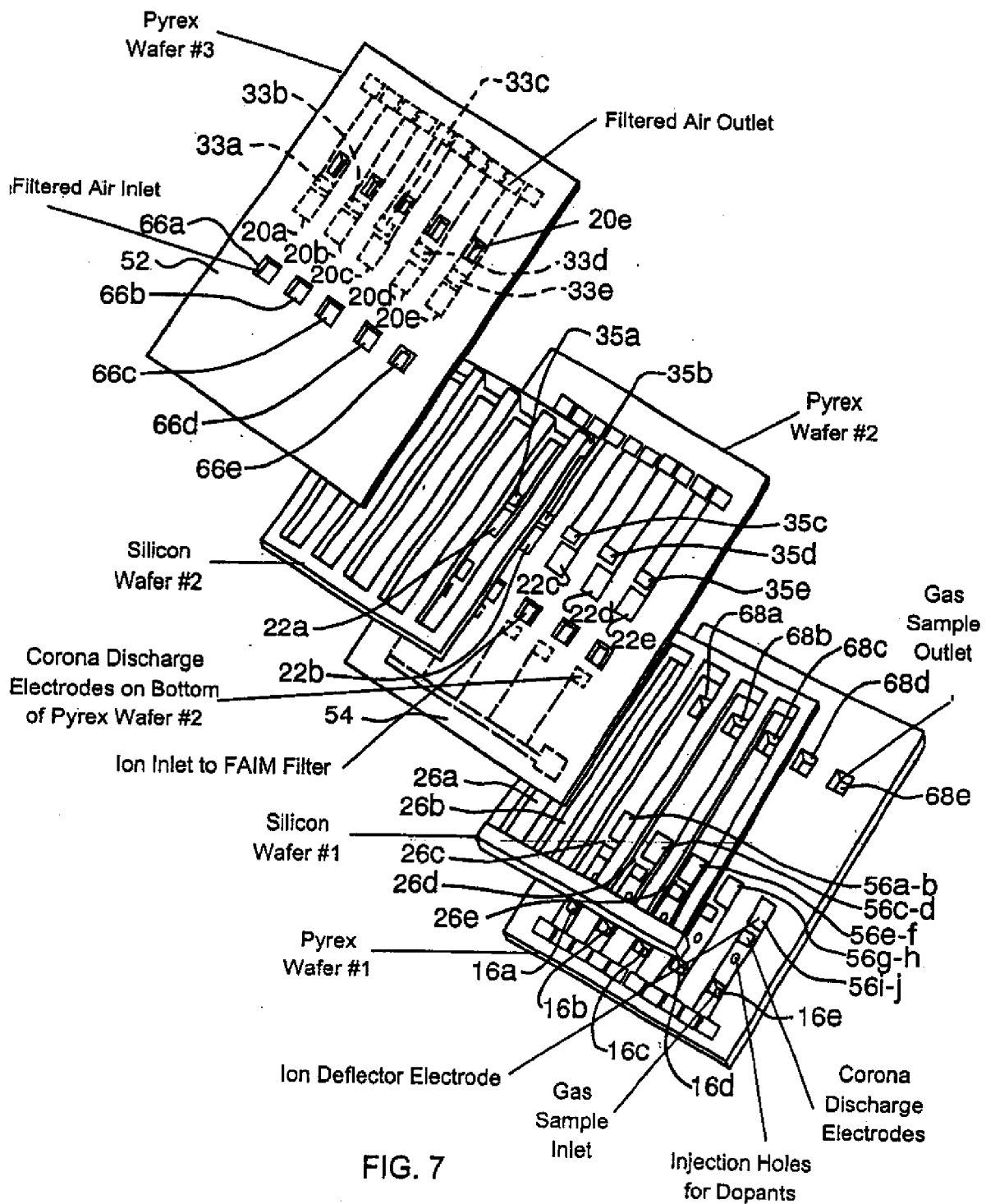

To improve FAIM spectrometry resolution even further, detector 32, FIG. 12, may be segmented. Thus, as ions pass through filter 24 between filter electrodes 20 and 22, the individual ions 38c'–38c'''' may be detected spatially, the ions having their trajectories 42c'–42c'''' determined according to their size, charge and cross section. Thus detector segment 32' will have one a concentration of one species of ion while detector segment 32'' will have a different ion species concentration, increasing the spectrum resolution as each segment may detect a particular ion species.

Although specific features of the invention are shown in some drawings and not in others, this is for convenience only as each feature may be combined with any or all of the other features in accordance with the invention.

Other embodiments will occur to those skilled in the art and are within the following claims:

What is claimed is:

1. A field asymmetric ion mobility system comprising:
   a housing having planar surfaces and defining a flow path between a sample input part and an output part;
   the housing formed with at least a pair of substrates that extend along the flow path; ions flowing from the vicinity of the input part toward the output part along the flow path;
   an ion filter disposed in the flow path for filtering of said ions, the filter including at least one pair of filter electrodes, at least one electrode on each substrate across from each other in the flow path; siad electrodes being insulated from each other via said substrates; and
   a control part configured for application of an asymmetric periodic voltage having alternating high and low field conditions to the ion filter electrodes for generating a filter field, said filter field for controlling the travel of said ions in said filter, said filter field being compensated to pass a species of said ions through said filter for detection.

2. The system of claim 1 wherein the substrates are glass.

3. The system of claim 2 wherein the substrates are separated by a spacer.

4. The system of claim 3 wherein the spacer is silicon and defines confining electrodes to focus the ions passing through the filter.

5. The system of claim 1 wherein the substrates are insulating and planar, and wherein the substrates form planar surfaces of said housing, said flow path accommodating flow of said ions in a carrier gas.

6. The system of claim 1 wherein the flow path is non-conducting and has conducting electrodes defined thereon.

7. The system of claim 1 wherein the substrate has insulating surfaces that define an electrically insulated flow path between the input part and the output part, the output part further comprising an ion detection region.

8. The system of claim 7 wherein the output part further includes a detector for detecting ions in the flow path.

9. The system of claim 7 wherein the ion detection region further includes at least a pair of detector electrodes disposed in the flow path, one electrode formed on each substrate, for detection of ions in the flow path.

10. The system of claim 9 wherein the control part is further configured to simultaneously independently enable detection of different ion species, the detected ions being representative of different detected ion species detected simultaneously by the detector electrodes.

11. The system of claim 9 wherein the control part defines electronic leads for applying signals to the electrodes.

12. The system of claim 1 wherein the output part further includes an array of detectors.

13. The system of claim 1 wherein the output part further includes a segmented detector, the detector formed by a plurality of electrodes placed along the flow path one after the other in the output part.

14. The system of claim 1 further comprising an array of ion filters, having at least one electrode formed on each substrate.

15. The system of claim 14 wherein all filters are assigned to the same flow path.

16. The system of claim 1 further comprising an array of ion filters, each having at least one electrode formed on each substrate, a separate flow path associated with each filter of the array, for passing ions in each flow path for simultaneous detection of ion species.

17. The system of claim 1 further comprising a source of ionized gas at the input part, a pump coupled to the substrate and communicating with the flow path for driving of the ionized gas from the source to the output part.

18. The system of claim 17 wherein the heater comprises a pair of electrodes, the electrodes having at least one additional function.

19. The system of claim 1 further comprising a recirculation pump coupled to the substrate and communicating with the flow path for recirculating gas in the flow path.

20. The system of claim 1 further comprising a heater, in the flow path, for heating the flow path and purging neutralized ions.

21. The system of claim 1 wherein the substrates are planar and extend to define the housing along the flow path.

22. The system of claim 1 further comprising an ion source for the input of ions into the flow path, the substrates forming an integral insulated housing along a flow axis of the flow path, the housing holding the ion source, ion filter, electronics part and output part in fixed relationship to the flow path axis.

23. The system of claim 22 wherein the control part includes an electrical connection for connection of the electrodes to an amplifier.

24. The system of claim 23, wherein a controller is defined within the housing for controlling ion filtering.

25. The system of claim 1 wherein the control part applies a bias voltage and the asymmetric periodic voltage across the ion filter electrodes for controlling the paths of ions through the filter.

26. The system of claim 1 wherein the control part further comprises a drive circuit for selectively adjusting the duty cycle of the periodic voltage to target a selected species of ion to be passed by the filter.

27. A field asymmetric ion mobility system comprising:
an input part and an output part;
a pair of insulative substrates defining between them a flow path for the flow of ions;
a pair of ion filter electrodes disposed opposite each other in the flow path, one electrode associated with each substrate;
an electronic controller input for applying of an asymmetric periodic voltage to the ion filter electrodes for controlling the path of said ions in the flow path; and the asymmetric periodic voltage being compensated for ion mobility to pass a desired species of said ions through said filter;
the insulative substrates electrically insulating the filter electrodes from the output part; and
ions in the flow path passing from the filter electrodes to the output part under control of the compensated applied asymmetric voltage.

28. The system of claim 27 wherein the substrates form an insulated flow path and are not held at a bias level.

29. The system of claim 28 wherein the substrates are planar and the insulated flow path electrically insulates the filter electrodes from the output part.

30. The system of claim 27 further comprising a detector defined in the output part downstream from the filter for detecting ions.

31. The system of claim 30 wherein the detector comprises detector electrodes, wherein the detector electrodes are independent of each other and the controller further comprising electrical leads for simultaneously outputting signals representing the specific ion species detected on each of the detector electrodes.

32. The system of claim 27 wherein the trajectory of an ion passing through the filter is regulated by the electronic controller, further comprising a segmented detector, downstream from the ion filter, its segments separated along the flow path to detect ions spatially according to their trajectories.

33. The system of claim 27 further comprising an array of electrodes, the electrodes being in the flow path and under the control of the electronic controller input.

34. The system of claim 33 further comprising a detector in the output part, said array comprising an array of filter electrodes, and the flow path being defined by a plurality of assigned flow paths, wherein pairs of the filter electrodes are associated with the assigned flow paths and are in communication with the detector part.

35. The system of claim 34 further comprising an array of detector electrodes, the detector array in communication with at least one pair of filter electrodes via the flow path.

36. The system of claim 27 wherein the output part further comprises a detection part, further comprising an ion source for ionizing a chemical sample and delivering ions from the sample into the flow path, the ions being filtered by the filter electrodes in the flow path and passing to the detection part for detection.

37. A field asymmetric ion mobility system comprising
an ion input part and a spectrometer part;
the spectrometer part having an ion filter part, an isolation part, and an output part, ions being delivered to the ion filter part by the input part;
the isolation part facilitating non-conductive connection of the filter part and the output part;
a flow channel extending from the filter part through the isolation part to the output part;

a controller part, the controller part for applying electrical potentials to the filter part, the electrical potentials including an asymmetric periodic voltage, for generating a control field;

said spectrometer part further comprising planar substrate surfaces opposite each other and each carrying an opposing electrode, the ion filter part including said opposing electrodes across from each other in the flow channel;

the flow channel defining a first flow path region for application of the control field to ions in the filter part, the ion filter part being located in the first flow path region;

the flow channel also defining a second flow path region, the isolation part being located in the second flow path region after the first region and before the output part;

the ion filter part passing ions in the flow channel under influence of the control field; and ions that are passed by the filter part traveling through the isolation part to the output part for detection, the isolation part isolating the control field from the output part.

38. The system of claim 37 further comprising a pair of substrates, the substrates defining the flow path, wherein the electrodes are electrically insulated and the substrates are electrically insulating.

39. The system of claim 38 wherein the substrates are planar.

40. A field asymmetric ion mobility system comprising:
an input part and a detector part;
cooperating spaced-apart substrates defining between them a flow path for the flow of ions;
a plurality of electrodes, including a pair of ion filter electrodes opposite each other and disposed in the flow path between the input part and detector part, one filter electrode associated with each substrate and defining an ion filter in the flow path;
the input part configured for receiving samples, the samples being ionized and comprised of a variety of ions, the ion filter for filtering the ions in the flow path;
the filter electrodes for application of an alternating asymmetric periodic voltage for generating a filter field with high and low field conditions, the filter field for controlling the travel of the ions in the filter, the filter field being compensated to pass selected ions through the filter;
the filter electrodes cooperating with the applied voltage and the flow path for simultaneously passing a selected plurality of the ions in the flow path to the detector part, the plurality of the ions including separate positive and negative ions;
the detector part enabling simultaneous detection of the separate positive and and negative ions; and
the detector part further configured for providing output information representative of this simultaneous detection.

41. The system of claim 40 wherein the detector part is formed with at least a pair of detector electrodes disposed in the flow path, at least one detector electrode is formed on one of the substrates, the detector electrodes carrying signals to independent outputs representative of the detected ion species, one detector electrode being held at a first level and the second detector electrode being held at a second level for simultaneous detection of a plurality of ion species passed by the filter.

42. The system of claim 40 wherein the plurality of electrodes comprises an array of filter electrodes formed on at least one of the substrates.

43. The system of claim 40 wherein the plurality of electrodes comprises an array of detector electrodes formed on at least one of the substrates.

44. The system of claim 40 wherein the plurality of electrodes further comprises a plurality of detector electrodes for detection of the separate positive and negative ions passed by the filter, further comprising an electronics part, the electronics part delivering the alternating asymmetric periodic voltage to the filter electrodes and providing separate independent simultaneous output signals representative of the detected separate positive and negative ions passed by the filter.

45. The system of claim 44 wherein the trajectory of the separate positive and negative ions passed by the filter is regulated by the electronics part, wherein the detector comprises a plurality of electrodes in sequence to form a segmented detector, downstream from the ion filter, its segments separated along the flow path to detect ions spatially according to their trajectories.

46. A field asymmetric ion mobility detection system comprising:
an input part and an output part,
at least a pair of spaced insulated substrates cooperating to define between them an enclosed planar flow path for the flow of ions from the input part to the output part;
a plurality of electrodes opposite each other and defined in the flow path the plurality defining at least one filter electrode associated with each substrate to form an ion filter section; and
an electronics part configured to apply controlling signals to the electrodes, and the electronics part applying an asymmetric periodic signal across the filter electrodes for filtering the flow of ions in the flow path, said filter being compensated to pass desired ion species out of the filter section.

47. The system of claim 46 wherein the substrates are planar and have at least insulated surfaces along the flow path between the filter electrodes and the output part.

48. The system of claim 46 further comprising a plurality of dedicated flow paths communicating with the output part, wherein the arrangement of electrodes comprises an array of filter electrode pairs associated with the dedicated flow paths.

49. The system of claim 46 further comprising a plurality of dedicated flow paths, wherein the arrangement of electrodes comprises an array of detector electrodes in the output part and in communication with the dedicated flow paths.

50. The system of claim 46 wherein the arrangement of electrodes comprises at least one pair of detector electrodes, one associated with each substrate, wherein the input part further comprises an ionization region and further comprising at least one electrode in the ionization region.

51. The system of claim 46 wherein the arrangement of electrodes further forms a segmented detector with several segments, each segment formed with at least one electrode on a substrate, the segments being formed in a longitudinal sequence along the flow path in the output part.

52. The system of claim 46 wherein the electronics part is further configured to sweep the applied controlling signals through a predetermined range according to the species being filtered.

53. The system of claim 46 wherein the substrates form a device housing, the device housing supporting the input part, flow path, output part, electrodes, and electronics part.

54. The system of claim 46 further comprising a flow pump for drawing a gas sample through the flow path from the input part to the output part.

55. The system of claim 46 further comprising a third substrate, wherein the substrates are planar and define two flow paths.

56. The system of claim 55 wherein the input part includes an ionization source for the ionization of gas samples drawn by the flow pump, further comprising a second pump for recirculation of air in at least one flow path.

57. A field asymmetric ion mobility system comprising:
a spacer extending along a longitudinal axis defining a flow path between a sample inlet and an outlet;
an ion filter disposed in the flow path and including a pair of spaced filter electrodes spaced apart by said spacer;
said ion filter further comprising substrate surfaces opposite each other and carrying said spaced filter electrodes; and
an electrical input supplying an asymmetric periodic voltage across the ion filter electrodes for generating a control field, the control field controlling the paths of ions traveling through the filter along the longitudinal axis toward the outlet.

58. The system of claim 57 wherein the spacer cooperates with the substrates to form a device housing enclosing the flow path.

59. The system of claim 57 wherein the outlet further comprises a detection area, the spacer defining a flow path extension extending along the longitudinal axis and connecting the input to the detection area, ions passed by the filter traveling to the detection area for detection.

60. The system of claim 59 wherein the detection area includes at least a pair of detector electrodes, further comprising an isolation part separating the ion filter from the detector, the isolating part isolating the control field from the detector electrodes.

61. The system of claim 57, wherein the spacer further defines longitudinal extensions, the flow path extending between the longitudinal extensions and extending along the spacer longitudinal axis.

62. The system of claim 57 further comprising a pair of substrates, the substrates cooperating with the spacer for defining the flow path between the inlet and outlet, the substrates further defining the filter electrodes facing each other across the flow path.

63. The system of claim 62 wherein the substrate has insulating surfaces that define an electrically insulated flow path portion between the inlet and the outlet, the outlet further comprising an ion detector.

64. The system of claim 57 wherein the spacer is silicon and defines confining electrodes in the flow path, further including a detector downstream from the ion filter for detecting ions traveling from the filter under control of the confining electrodes.

65. The system of claim 57 wherein the outlet further includes a detector, the detector formed with at least a pair of electrodes for detection of ions in the flow path, wherein the controller further defines electronic leads for applying signals to the electrodes.

66. The system of claim 57 wherein the outlet defines an array of detectors, the detectors formed each with a pair of electrodes disposed in the flow path for detection of ion species passed by the filter.

67. The system of claim 57 wherein the outlet comprises a detector, the detector comprising a pair of ion detector electrodes, wherein the electronics part is further configured to simultaneously independently enable detection of different ion species, the detected ions being representative of different detected ion species detected simultaneously by the detector, the electronics part including separate output leads from each detector electrode.

68. The system of claim 57 in which the outlet comprises a detector having a plurality of electrode segments, the segments separated along the flow path to spatially separate detection of ions according to their trajectories.

69. The system of claim 57 wherein the ion filter comprises an array of filters, each filter comprising a pair of electrodes in the flow path.

70. The system of claim 57 wherein the flow path is planar.

71. The system of claim 57 further comprising a source of ions at the inlet, a pump communicating with the flow path for driving of the ions through the filter.

72. The system of claim 57 further comprising a heater, in the flow path, for heating the flow path and purging neutralized ions.

73. The system of claim 72 wherein the heater comprises a pair of electrodes, the electrodes having at least one additional function.

74. The system of claim 73 wherein the heater electrodes include the ion filter electrodes.

75. A micromechanical field asymmetric ion mobility filter for a detection system comprising:
a pair of spaced planar substrates defining between them a flow path between a sample inlet and an outlet;
an ion filter disposed in the path, further including at least a pair of spaced electrodes, the filter comprising at least one of the electrodes on each substrate opposite each other;
an electrical controller for applying voltages, including an asymmetric periodic voltage applied to the filter, for controlling the paths of ions through the filter; and
a heater for heating the flow path.

76. The system of claim 75 wherein said pair of the electrodes on the substrates is used as a heat source for the heater, the electrical controller configured to deliver a heater signal to the heat source.

77. The system of claim 76 wherein the electrical controller is configured to selectively apply a current through the filter electrodes to generate heat.

78. The system of claim 76 wherein the electrodes further define a pair of detector electrodes.

79. The system of claim 75 wherein the filter electrodes are a heat source for the heater, the electrical controller configured to deliver a bias voltage and a heater voltage to the filter electrodes.

80. A field asymmetric ion mobility filter system comprising:
a flow path extending between a sample inlet and an outlet;
an ion filter disposed in the flow path;
said ion filter further comprising electrodes opposite each other;
an electrical controller configured to apply an asymmetric periodic voltage across the ion filter electrodes for controlling the path of ions through the ion filter; and
a selection circuit configured for selectively adjusting the duty cycle of the asymmetric periodic voltage to enable ion species from the sample inlet to be separated, with desired species being passing through the filter for detection.

81. The ion mobility filter of claim 80 wherein the asymmetric periodic voltage is not compensated with a bias voltage, further including a detector downstream from the ion filter for detecting ion species that are passed by the filter.

82. In an ion mobility filter system having a flow path that defines an ion inlet, an output, and an ion filter with opposed electrodes in the flow path between the inlet and the output, the filter passing ions flowing from the inlet to the output, a method for filtering ions, the method comprising the steps of:

applying an asymmetric periodic voltage to the ion filter for generating a filter field for controlling the path of ions in the filter between the electrodes, providing the field with high and low field conditions, adjusting the duty cycle of the asymmetric periodic voltage to enable ion species to be separated by the filter according to differences in their mobilities in said high and low field conditions, and passing species of said ions through the filter according to the duty cycle for detection of said species at the output part.

* * * * *

UNITED STATES PATENT AND TRADEMARK OFFICE
CERTIFICATE OF CORRECTION

PATENT NO. : 6,495,823 B1
DATED : December 17, 2002
INVENTOR(S) : Raanan A. Miller and Erkinjon G. Nazarov It is certified that error appears in the above-identified patent and that said Letters Patent is hereby corrected as shown below:

Column 8,
Line 44, delete "siad" and insert -- said --

Column 10,
Line 6, delete "disposed"
Line 10, delete "to" and insert -- across --
Line 11, delete ";" and insert -- , --
Line 11, delete "and"

Column 11,
Line 54, delete "enabling" and insert -- configured for --
Line 55, delete "and"
Line 55, after "ions" insert -- passed by the filter --

Column 13,
Line 23, after the second "control field" insert -- being compensated for --

Column 16,
Line 3, delete "between the electrodes"
Line 6, delete "by the filter"

Signed and Sealed this

Second Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,495,823 B1
DATED : December 17, 2002
INVENTOR(S) : Raanan A, Miller and Erkinjon G. Nazarov It is certified that error appears in the above-identified patent and that said Letters Patent is hereby corrected as shown below:

<u>Title page,</u>
Item [56], References Cited, U.S. PATENT DOCUMENTS, change "6,188,167" to -- 6,188,067 --

<u>Column 15,</u>
Line 8, cancel Claim 82.

Signed and Sealed this

Seventeenth Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO.   : 6,495,823 B1
DATED        : December 17, 2002
INVENTOR(S)  : Miller et al.

It is certified that error appears in the above-identified patent and that said Letters Patent is hereby corrected as shown below:

Drawings,
Sheet 8 of 13, replace Figure 7 with the following version:

Signed and Sealed this

Second Day of August, 2005

JON W. DUDAS
*Director of the United States Patent and Trademark Office*